United States Patent [19]
Kolb et al.

[11] Patent Number: 5,150,373
[45] Date of Patent: Sep. 22, 1992

[54] DEVICE FOR RINSING A HOLLOW GUIDE FOR CARBON DIOXIDE LASERS

[75] Inventors: Achim Kolb, Bretten; Manfred Baier, Knittlingen; Klaus Müller, Knittlingen-Freudens, all of Fed. Rep. of Germany

[73] Assignee: Richard Wolf GmbH, Knittlingen, Fed. Rep. of Germany

[21] Appl. No.: 668,026

[22] Filed: Mar. 12, 1991

[30] Foreign Application Priority Data

Mar. 15, 1990 [DE] Fed. Rep. of Germany ....... 4008217

[51] Int. Cl.$^5$ ............................................. H01S 3/03
[52] U.S. Cl. ...................................... 372/61; 372/34; 372/58; 372/59; 372/65
[58] Field of Search ................. 372/34, 65, 61, 59, 372/58, 55

[56] References Cited

U.S. PATENT DOCUMENTS

| | | | |
|---|---|---|---|
| 3,784,927 | 1/1974 | Rudolph | 372/65 |
| 4,365,335 | 12/1982 | Lamboo | 372/61 |
| 4,519,390 | 5/1986 | Horne | 128/303.1 |
| 4,592,353 | 6/1986 | Daikuzono | 128/303.1 |
| 4,823,356 | 4/1889 | Riley | 372/61 |
| 4,866,726 | 9/1989 | Ortiz et al. | 372/65 |
| 5,020,070 | 5/1991 | Lombardo | 372/65 |

FOREIGN PATENT DOCUMENTS 7709964 7/1977 Fed. Rep. of Germany .
7810089 7/1978 Fed. Rep. of Germany .

OTHER PUBLICATIONS

Frank, F. Waveguide-Laser, die neue CO$_2$-Laser Generation, *Laser Brief* (1985), a publication of MBB Laser-Therapie Systems and Translation thereof.

*Primary Examiner*—Georgia Y. Epps
*Attorney, Agent, or Firm*—Cohen, Pontani Lieberman & Pavane

[57] ABSTRACT

The hollow guide is designed as a thin ceramic hollow tube which is guided in an outer tube while leaving a hollow space between the outer tube and the ceramic hollow tube, the outer tube being provided at its proximal end with a connecting part having a gas connection and receiving a focusing optical system. The ceramic hollow tube is guided in the outer tube through at least one mounting part arranged at the proximal end and at least one mounting part at the distal end, which in each case is supported locally with respect to the inner wall of the outer tube. The mounting parts are thus arranged so that free flow cross-sections to conduct the rinsing gas remain in the region of support, these being matched with the internal inner cross-section of the ceramic hollow tube, so that gas flow flowing past the ceramic hollow tube is produced both on the outside and on the inside. The gas flow effects cooling of the ceramic hollow tube on the one hand and prevents impurities penetrating the distal end of the ceramic hollow tube on the other hand.

12 Claims, 1 Drawing Sheet

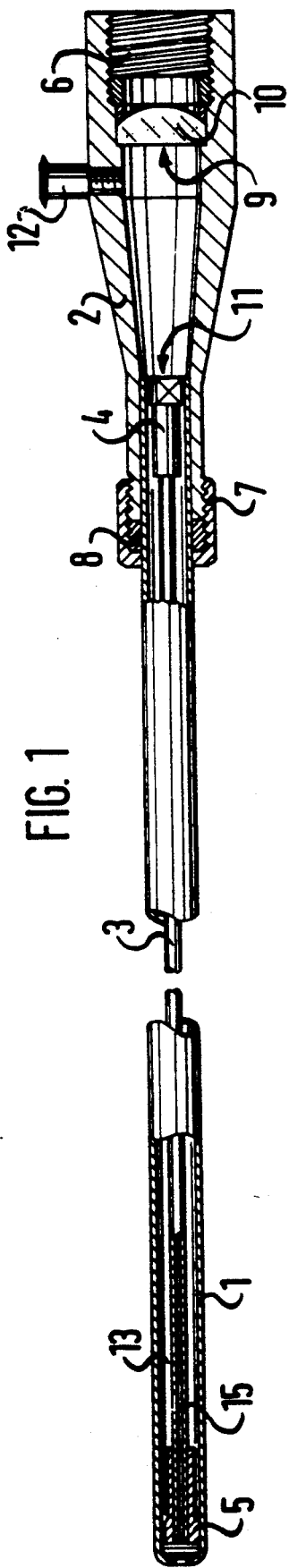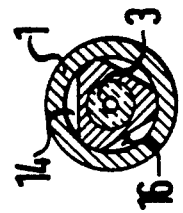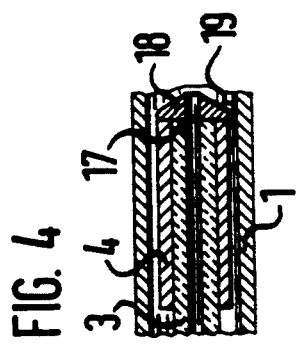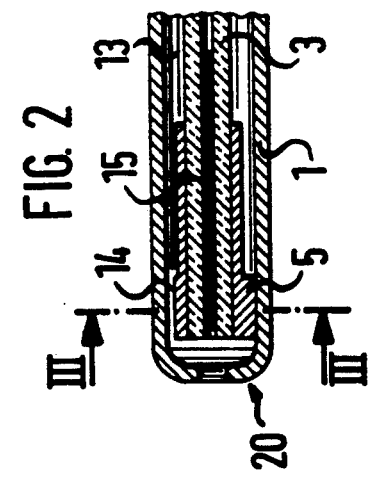

DEVICE FOR RINSING A HOLLOW GUIDE FOR CARBON DIOXIDE LASERS

BACKGROUND OF THE INVENTION

A) Field of the Invention

The invention relates to a device for gas rinsing a hollow guide for $CO_2$ lasers, the hollow guide being designed as a thin ceramic hollow tube which is guided within an outer tube, preferably made from stainless steel, while leaving a hollow space between the latter and the hollow ceramic tube, and the outer tube being provided on the proximal side with a connecting part having a gas connection and a part for receiving a focusing optical system.

B) Description of the Prior Art

Lasers are frequently used in medicine for diagnosis and therapy or for surgical purposes. In recent years the $CO_2$ laser has thus been successful, in particular in gynecology, and is used in this field particularly in laparoscopy, to remove, for example, growths on the uterus or on the ovaries. A particular advantage of this method is in the ability to work largely in a blood-free manner, as small blood vessels are immediately coagulated due to the thermal effect of the laser beam. More recently so-called hollow guides are used as applicators for $CO_2$ laser therapy, which are introduced by means of a trocar sleeve, for example into the abdominal cavity of a female patient. Hollow guides of this type consist of a thin hollow ceramic tube, which is encased in a stainless steel tube for reasons of stability, and a coupling component containing a convex lens made from zinc selenide. The lens serves to focus the laser beam on the inlet orifice of the hollow ceramic tube.

One problem in using such hollow guides results from the fact that they may become very hot, especially when using a high performance laser, and when used for a long period of therapy. This heating poses a danger; this is a danger to the user and the patient and may also lead to destruction of the hollow guide. Heating of the hollow guide is caused by the multiple reflections resulting from the geometry of the beam and absorptions associated with them on the wall of the hollow tube. Furthermore, steam and burnt gas produced when the laser is directed at body fluid and during coagulation and cutting with the laser beam, may penetrate the distal region of the ceramic hollow tube. These impurities absorb the laser energy particularly strongly and may thus lead to very high heating of the hollow guide and hence cause an immediate danger for the patient.

Hollow guides must therefore be intensively cooled and kept free of impurities to ensure their safe and effective use. For this purpose hollow guides are conventionally connected to $CO_2$ gas rinsing systems having adjustable flow rates, by means of a rinsing gas connection, such as may be seen for example from the instructions for use for a hollow guide for a $CO_2$ laser transmission system from Messrs. Heraeus. Differing flow rates are required for the protection from, or for the removal of, impurities, depending on the diameter of the hollow guide.

Rinsing impurities away from the hollow tube is known, for example from German utility model 7810089. Furthermore, German utility model 1810089 and German utility model 7709964 also describe advantageous possibilities for rinsing the distal connecting element when using a laser in conjunction with a lens system or a laser fiber. In this process, the distal connecting element is rinsed by introducing the gas stream to the distal end of the guide tube past the guide tube which receives the lens system or the laser fiber. The guide tube is surrounded by an outer tube for this purpose and the distal end of the outer tube may be rolled in to divert or direct the gas stream to the distal connecting element.

Impurities, at the distal connecting element of hollow guides having optical systems, or impurities in the interior of hollow tubes can be avoided or removed in this manner. The hollow tubes are also cooled in this manner.

However, the disadvantage of using the hollow guides according to the state of the art is that steam and smoke produced in a body cavity, and impairing the view of the user when working with the laser, cannot be adequately removed from the area of application using the gas flow rates which can be achieved using hollow guides according to the state of the art. Therefore additional gas rinsing devices, which can be introduced into the body cavity by means of an additional incision, are always required when using a hollow guide in body cavities in order to be able to provide a good view for the operator.

OBJECT OF THE INVENTION

It is an object of the present invention to provide a hollow guide with which it is possible to always provide a clear view in the area of application of the laser beam, so that an additional gas rinsing device is not necessary, and at the same time to guarantee the necessary cooling of the hollow guide and to ensure that the hollow tube is always rinsed clear of impurities.

SUMMARY OF THE INVENTION

To this end, the present invention consists of a device for gas rinsing a hollow guide for $CO_2$ lasers, the hollow guide being designed as a thin hollow ceramic tube which is guided in an outer tube, preferably made from stainless steel, while leaving a hollow space between the outer and the hollow ceramic tube. The outer tube is being provided on the proximal side with a connecting part having a gas connection and a part for receiving a focusing optical system, characterised in that the hollow ceramic tube is guided in the other tube through at least one mounting part arranged on the proximal side and at least one mounting part on the distal side, which in each case are supported locally with respect to the inner wall of the outer tube, and are provided with free flow cross-sections to conduct the rinsing gas in the region of support.

By means of the apparatus of the present invention, the gas connection may be arranged in the region between the focusing optical system and the proximal end of the hollow ceramic tube, and the flow cross-sections may have dimensions in the region of the mounting parts to be matched with the internal cross-section of the hollow ceramic tube, so that gas flow occurs both in the latter and in the hollow space between the ceramic hollow tube and the outer tube.

Gas flows past the hollow ceramic tube on the inside and on the outside in this manner and hence the latter is adequately cooled. At the same time the gas flow in the interior of the ceramic hollow tube prevents impurities from penetrating the hollow tube. This effect may be increased by designing the outer tube to be rolled inwards at its distal end, so that the gas flow flowing externally of the ceramic hollow tube is diverted to the distal end of the hollow tube.

In order to avoid damage to the hollow tube when the laser beam is not coupled in an ideal manner to the same, the proximal side end of the ceramic hollow tube may be provided with a conical head part which is provided with a bore aligned with the interior hollow space of the ceramic hollow tube.

BRIEF DESCRIPTION OF THE DRAWINGS

The foregoing summary of the invention as well as the following detailed description of preferred embodiments, will be better understood when read in objection with the appended drawings. For the purpose of illustrating the invention, there are shown in the drawings embodiments which are presently preferred, it being understood, however, that the invention is not limited to the specific arrangement and instrumentalities disclosed.

FIG. 1 shows a hollow guide and is represented partially in section.

FIG. 2 is a longitudinal section through a distal end region of the hollow guide according to FIG. 1, FIG. 3 is a cross-section taken along the line III—III of FIG. 2, FIG. 4 is a longitudinal section through a proximal end region of the hollow guide according to FIG. 1, FIG. 5 is an end view of the hollow guide shown in FIG. 4, and FIG. 6 is a cross-section taken along the line III—III of FIG. 2 of a modified embodiment of the distal end region of the hollow guide.

DETAILED DESCRIPTION OF THE PREFERRED EMBODIMENT

According to FIG. 1, a hollow guide comprises an outer tube 1 having a connecting part 2 at its proximal end and a ceramic hollow tube 3 guided in the outer tube 1. The hollow ceramic tube 3 is guided in the region of its ends through a mounting part 4 arranged on the proximal end and mounting part 5 arranged on the distal end, so that the hollow ceramic tube 3 and the outer tube 1 extend coaxially with one another and at a distance from one another.

The connecting part 2 serves to optically couple the hollow ceramic tube 3 to a mirror pivot arm of a laser system, and has a coupling region 6 on the proximal end for this purpose, which can also be connected to an adapter appropriate to the mirror pivot arm of the particular laser system used. The connecting part 2 and the outer tube 1 may be connected by means of a union nut 7 which overlaps a part 8, connected rigidly to the outer tube. The part 8 ensures that the proximal inlet orifice of the hollow tube lies in the focus of the lens 10.

The connecting part 2 contains a focusing optical system 9 comprising a convex lens 10, for example made from zinc selenide, fixed in this part in a gas-tight manner, and which serves to focus the laser beam on the proximal orifice 11 of the hollow ceramic tube 3 so that the laser beam having an optical axis aligned virtually parallel to the geometric axis of the hollow ceramic tube may enter the orifice 11 of the ceramic hollow tube 3. The connecting part 2 is also provided with a gas connection 12, for example a Luer connection, which opens into the space between orifice 11 of the ceramic hollow tube 3 and the convex lens 10, and can be connected to a gas supply device (not shown) for gas rinsing and cooling of the hollow guide.

The hollow ceramic tube 3 is provided with at least two mounting parts 4 or 5, one of which is located at the distal end and one at the proximal end of the ceramic hollow tube 3, for central positioning of the hollow tube 3 in the outer tube 1, and to keep a hollow space 13 free between ceramic hollow tube 3 and outer tube 1. The mounting parts 4 and 5 are arranged so that they receive the ceramic hollow tube 3 and fix it in a position in the outer tube 1, in which hollow spaces 14 (FIG. 3) are retained between the outer tube 1 and the mounting parts. The gas flow necessary to keep the user's view clear in the area of application may thus be passed through the hollow spaces 13 and 14. At the same time the gas flow necessary to cool the hollow tube 3 and to keep the same free from impurities may be maintained through interior hollow space 15 of the hollow tube 3.

The flow impedance in the hollow space 13 can be changed by the number of mounting parts and by the axial extension of the mounting parts, as well as by alternating the hollow spaces 14, at the pre-stated internal and external diameter of ceramic hollow tube 3 and outer tube 1. It is thus possible to vary the ratio of the gas flows through the two hollow spaces 13 and 15, so that the gas stream through the interior hollow space 15 required for cooling and rinsing the hollow tube 3 free of impurities may also always be ensured. It should be noted that the ratio of flow through the hollow space 13 and hollow ceramic tube 3 can be varied by mechanically varying the gas flow path, or by varying a parameter of the gas flow, such as a pressure waveform. Of course, it will be realized that when the impedance to gas flow is matched between the hollow space 13 and the hollow ceramic tube, the gas flows will also be equal.

The mounting parts 4 and 5 are rigidly connected to the ceramic hollow tube 3, for example by adhesion. The adhering point of the proximal mounting part 4 is advantageously arranged at a distance away from the proximal orifice 11, which is the coupling point of the laser beam and which becomes very hot when the laser beam in operation.

Only the proximal mounting part 4 is connected rigidly to the outer tube 1 to prevent damage to the ceramic hollow tube 3 as a result of tensile and pressure stresses which may occur due to temperature variations. Hence, the hollow ceramic tube 3 having the distal mounting part 5, or possibly further mounting parts attached between distal and proximal ends of the ceramic hollow tube 3 attached to it may allow carry out, when temperature is varied, the necessary length extensions (thermal expansion) in the outer tube 1, so that tensile and pressure stresses are reduced.

In principle, the distal and the proximal mounting parts 4 or 5 and possibly further mounting parts may be designed as shown in FIGS. 2 and 3. As can be seen from the figures mentioned, the mounting part is, for example, a turned part having a diameter corresponding to the internal diameter of the outer tube 1, which is provided with bevelled surfaces 16 and a penetrating bore. The diameter of the bore corresponds here to the external diameter of the hollow tube 3 and is used for receiving the same.

It is possible that the laser beam at the coupling point does not meet the orifice 11 of the hollow tube 3 in an ideal manner. However when using a mounting part according to FIG. 2 as a proximal mounting part 4, it is directed on the end face 17 of the hollow tube 3 and damages the and face 17. A mounting part 4 having a bevelled surface 16, as shown in FIGS. 4 and 5, and in which the proximal end face 17 is covered by means of a head part 18, and hence protected from the laser beam, is therefore used as a proximal mounting part. The mounting part 4 also has a bore, but it is recessed; that is it has a diameter corresponding to the external diameter of the hollow ceramic tube 3 and serves to receive the hollow ceramic tube 3 over a part of the length of the mounting part 4, and which continues over the rest of the length with a diameter corresponding to the internal inner diameter of the hollow tube 3. The head part 18 of the mounting part 4 is also provided with a conical surface 19 on the proximal side. Laser rays which do not pass into the hollow tube 3 but meet the proximalside end faces 19 of the head part 18 are thus reflected so that they are not directed back into the mirror pivot arm of the laser system. If the surfaces 19 were directed parallel with respect to the hollow guide axis, the laser rays reflected back into the laser system via the mirror pivot arm could lead to damage in the laser system which could lead to the laser being cut off.

The spaced arrangement of the hollow ceramic tube 3 in the outer tube 1 achieved with the aid of the mounting parts 4 and 5 discussed above, which not only ensures that, when using the laser, a good view in the area of application can always be provided by means of the gas flow in the external hollow space 13, but also that cooling of the hollow tube 3 is also considerably improved by means of this gas flow. The removal of impurities at the distal end of the hollow tube is also considerably improved by means of this external gas stream, in particular when the outer tube 1 is rolled-in at its distal end 20, as a result of which a high flow rate for the rinsing gas is achieved at the laser beam outlet point.

As described, the ratio of the gas streams in the two hollow spaces 13 and 15 is varied by the number and the arrangement of the mounting parts, depending on the hollow ceramic tube 3 used, to ensure the gas flow through the interior hollow space 15 required for cooling the hollow tube 3. Hence a mounting part may be designed, for example as also shown in FIG. 5, where the ceramic hollow tube 3 is centred by means of spacing wires 21, attached to it.

It should be understood that the preferred embodiments and examples are for illustrative purposes only, and are not to be construed as limiting the scope of the present invention.

The present invention may be embodied in other specific forms without departing from the spirit or essential attributes thereof and, accordingly, reference should be made to the appended claims, rather than to the foregoing specification as indicating the scope of the invention.

We claim:

1. A device for gas rinsing a hollow guide for $CO_2$ lasers, comprising a hollow guide being designed as a thin ceramic hollow tube which has proximal and distal ends and which is guided in an outer tube, made from stainless steel, whilst leaving a hollow space between the outer tube and the ceramic hollow tube, with the outer tube having an inner wall, proximal and distal ends and being provided at the proximal end with a connecting part having a gas connection and receiving a focusing optical system, wherein the ceramic hollow tube is guided in the outer tube through at least one mounting part arranged at the proximal end and at least one mounting part at the distal end, which in each case is supported locally with respect to the inner wall of the outer tube and is provided with free flow cross-sections to conduct the rinsing gas in the region of support.

2. A device according to claim 1, wherein the gas connection is arranged in a region between the focusing optical system and the proximal end of the ceramic hollow tube, and wherein the flow cross-sections have dimensions in the region of the mounting parts which match the internal cross-section of the ceramic hollow tube, so that gas flow occurs both in the ceramic hollow tube and in the hollow space between the ceramic hollow tube and the outer tube.

3. A device according to claim 1, wherein the outer tube is rolled inwards at its distal end.

4. A device according to claim 1, wherein said ceramic hollow tube comprises a proximal end, a distal end, an interior hollow space and a conical head part of said proximal end, having a bore, wherein said bore is axially aligned with said interior hollow space of said ceramic hollow tube.

5. A device for rinsing a hollow guide for $CO_2$ lasers, comprising:
   (a) a hollow ceramic tube comprising a bore, an inner surface and an outer surface;
   (b) an outer tube, into which said hollow ceramic tube is inserted, said hollow ceramic tube and said outer tube being arranged such that there is a space for gas communication between said hollow ceramic tube and said outer tube;
   (c) a plurality of mounting parts, each having a proximal side and a distal side, arranged to locate said said hollow ceramic tube within said outer tube in a mounting region so that there is a contiguous space for gas communication between the proximal side and the distal side of each of said mounting parts,
   thereby allowing a flow of a rinsing gas in said space for gas communication and said contiguous space.

6. A device according to claim 5, wherein said outer tube comprises a stainless steel tube.

7. A device according to claim 5, wherein said outer tube comprises a proximal end and a distal end, wherein said proximal end comprises a gas connection and an optical system.

8. A device according to claim 5, comprising two mounting parts, one for mounting a proximal end of the hollow ceramic tube and one for mounting a distal end of the hollow ceramic tube.

9. A device according to claim 7, wherein said proximal end of said hollow ceramic tube is located within the outer tube, and said gas connection is arranged between said optical system and said proximal end of said hollow ceramic tube.

10. A device according to claim 5, wherein an impedance of a flow of a rinsing gas in said space for gas communication and said contiguous space is matched to an impedance of a flow of a rinsing gas in said bore of said hollow ceramic tube.

11. A device according to claim 5, wherein said outer tube comprises a distal end having a gas deflecting portion, whereby said rinsing gas is deflected toward said distal end of said hollow ceramic tube.

12. A device according to claim 5, wherein said hollow ceramic tube comprises a bore, an inner surface, an outer surface, a proximal end, a distal end and a conical head part of said proximal end, wherein said bore is axially aligned with said interior hollow space of said hollow ceramic tube.

* * * * *